(12) United States Patent
Faltys et al.

(10) Patent No.: US 6,272,382 B1
(45) Date of Patent: Aug. 7, 2001

(54) FULLY IMPLANTABLE COCHLEAR IMPLANT SYSTEM

(75) Inventors: Michael A. Faltys, Northridge, CA (US); Janusz A. Kuzma, Englewood, CO (US); Thomas H. R. Lenarz, Hannover (DE); Alfred E. Mann, Hollywood, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/407,826

(22) Filed: Sep. 28, 1999

Related U.S. Application Data

(63) Continuation-in-part of application No. 09/126,615, filed on Jul. 31, 1998, now Pat. No. 6,067,474.
(60) Provisional application No. 60/108,923, filed on Nov. 17, 1998.

(51) Int. Cl.[7] .................................................. A61N 1/36
(52) U.S. Cl. .................................................. 607/57
(58) Field of Search ........................... 607/55, 56, 57, 607/137; 600/25

(56) References Cited

U.S. PATENT DOCUMENTS

| | | |
|---|---|---|
| 3,942,535 | 3/1976 | Schulman ............................ 128/419 |
| 4,495,917 | 1/1985 | Byers .................................. 128/419 |
| 4,516,820 | 5/1985 | Kuzma .................................. 339/48 |
| 4,532,930 | 8/1985 | Crosby et al. ....................... 138/419 |
| 4,592,359 | 7/1986 | Galbraith ............................. 128/419 |
| 4,764,132 | 8/1988 | Stutz, Jr. ............................. 439/810 |
| 5,626,629 | 5/1997 | Faltys et al. ............................ 607/57 |
| 5,776,172 | 7/1998 | Schulman et al. ..................... 607/57 |
| 5,881,158 | 3/1999 | Lesinski et al. ..................... 381/174 |

*Primary Examiner*—Scott M. Getzow
(74) *Attorney, Agent, or Firm*—Bryant R. Gold

(57) ABSTRACT

The present invention provides a fully implantable cochlear implant system (FICIS) that allows various configurations of different modules to be combined so as to meet the needs of a particular patient, including very young patients. At least three main modules are used in the FICIS, including (1) a small implantable cochlear stimulator (ICS) module, with permanently attached cochlear electrode array; (2) an implantable speech processor (ISP) module, with integrated microphone and rechargeable battery; and (3) an external module. In one embodiment, the external module may comprise an external speech processor (ESP) module. In another embodiment, the external module may comprise an external battery charger (EBC) module. The ICS and ISP modules are configured to facilitate long time reliable use of the ICS module, e.g., for the lifetime of the patient, and low-risk, relatively easy replacement of the ISP module.

13 Claims, 12 Drawing Sheets

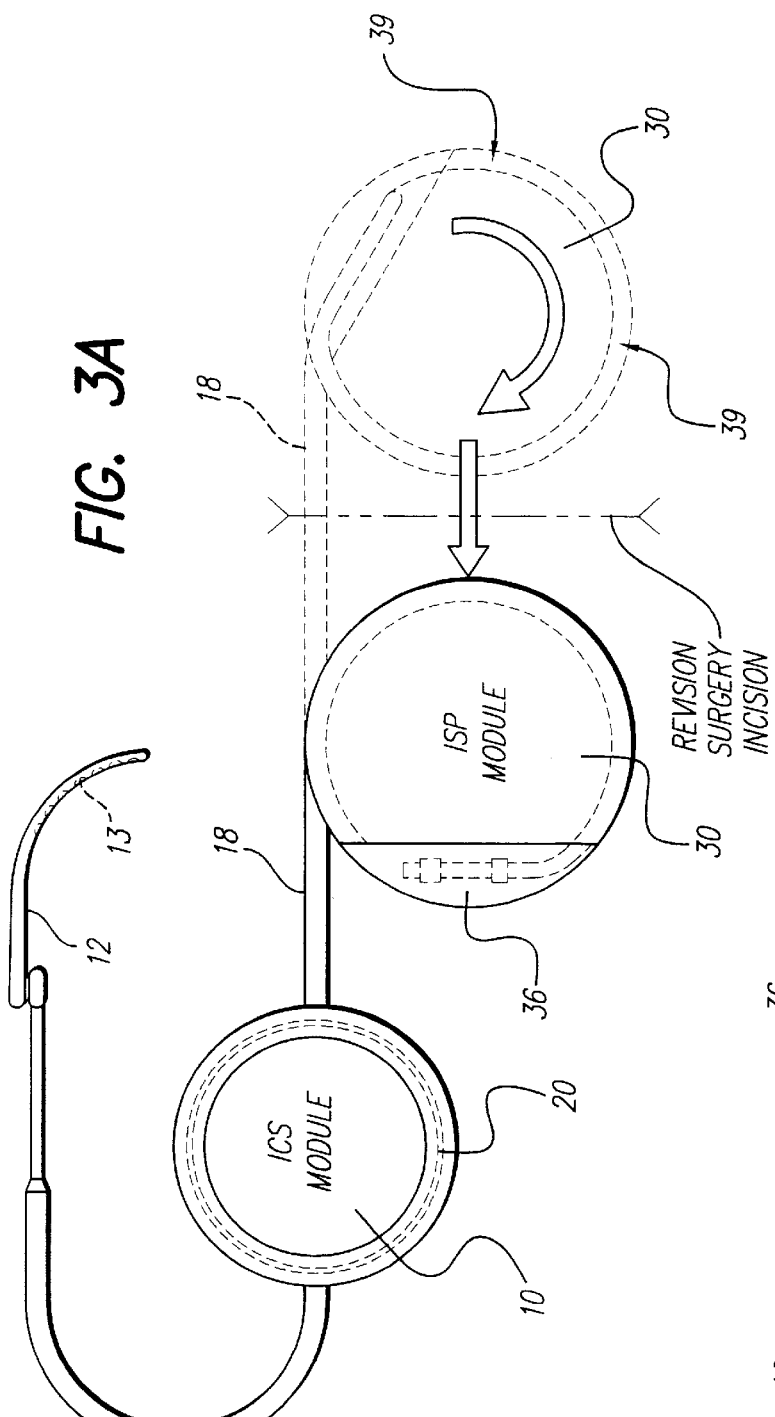
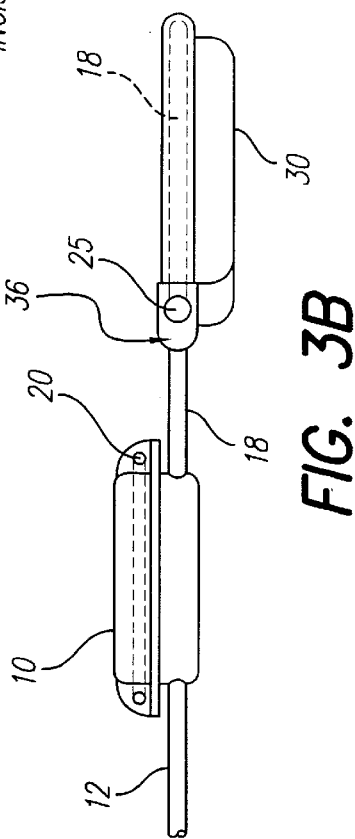
FIG. 3A
FIG. 3B

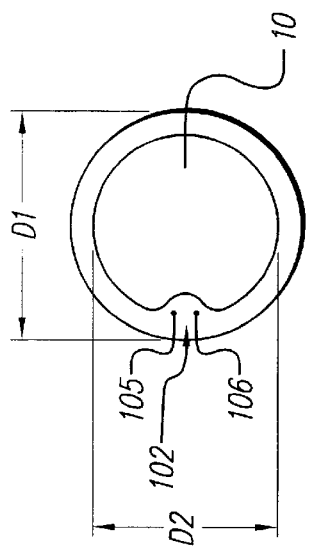
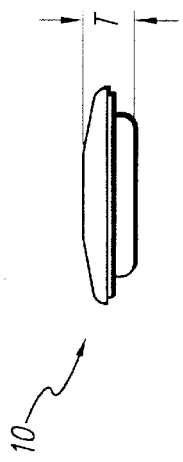
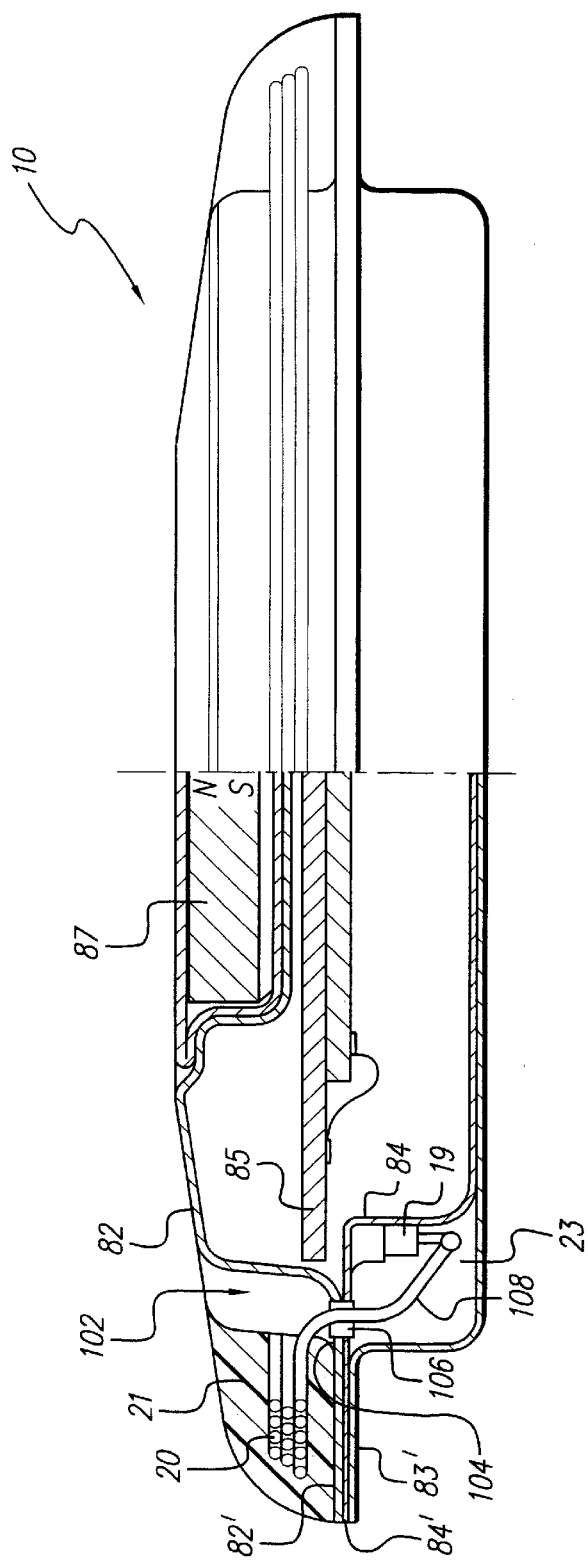

FULLY IMPLANTABLE COCHLEAR IMPLANT SYSTEM

RELATED APPLICATIONS

The present provisional application is a continuation-in-part (CIP) of application Ser. No. 09/126,615, filed Jul. 31, 1998 U.S. Pat. No. 6,067,474, and further claims the benefit of U.S. Provisional Patent Application Ser. No. 60/108,923, filed Nov. 17, 1998.

FIELD OF THE INVENTION

The present invention relates to implantable devices, and more particularly, to a fully implantable device or system for stimulating or sensing living tissue wherein the implantable device may include a rechargeable battery or other replenishable power source. More particularly, the present invention relates to a fully implantable cochlear implant system (FICIS) that allows profoundly deaf persons to hear sounds without the need for wearing or carrying external (non-implanted) hearing devices or components. A key feature of the invention relates to partitioning the circuit functions within the FICIS in separate modules that facilitate upgrading circuit functions, adapting the system to a range of head sizes and shapes, and/or replacing, through minimal invasive surgery, the battery or power source used within the FICIS. Another feature of the invention relates to a FICIS that may be operated with conventional external (non-implanted) components of a cochlear stimulation system, e.g., with an external speech processor or an external battery charger, when needed or desired.

BACKGROUND OF THE INVENTION

Presently available implantable stimulation devices, such as a cochlear implant device or a neural stimulator, typically have an implanted unit, an external ac coil, and an external control unit and power source. The external control unit and power source includes a suitable control processor and other circuitry that generates and sends the appropriate command and power signals to the implanted unit to enable it to carry out its intended function. The eternal control unit and power source is powered by a battery that supplies electrical power through the ac coil to the implanted unit via inductive coupling for providing power for any necessary signal processing and control circuitry and for electrically stimulating select nerves or muscles. Efficient power transmission through a patient's skin from the external unit to the implanted unit via inductive coupling requires constant close alignment between the two units.

Representative prior art cochlear implant systems are disclosed, e.g., in U.S. Pat. Nos. 4,532,930; 4,592,359; 4,947,844 and 5,776,172, all of which are incorporated herein by reference.

Disadvantageously, each of the known prior art cochlear stimulation systems requires the use of an external power source and speech processing system, coupled to the implanted stimulation device. For many patients, achieving and maintaining the required coupling between the external components and the implanted component can be troublesome, inconvenient, and unsightly. Thus, there exists a need and desire for a small, lightweight fully implantable device or system that does not require an external unit in order to be fully functional, that does not need constant external power, and that includes a long-lasting internal battery that may be recharged, when necessary, within a relatively short time period.

Moreover, even if a rechargeable battery were available for use within an implantable cochlear stimulation system, such rechargeable battery must not significantly alter the size of the existing implantable cochlear stimulator. This is because the curvature and thickness of the skull is such that there is only a limited amount of space wherein a surgeon may form a pocket wherein a cochlear stimulator may be implanted. This is particularly an acute problem for young children, where the thickness of the skull is relatively thin and the curvature of the skull is greater than for an adult. Thus, there is a need for a fully implantable cochlear implant system that is adaptable and lends itself for implantation within a range of head sizes and shapes.

Additionally, even where a rechargeable battery is employed within a fully implantable cochlear implant system, which fully implantable system includes an implantable speech processor and microphone, it may be necessary or desirable, from time to time, to replace the battery and/or to upgrade the speech processor hardware. Because implantation of the cochlear implant system, including insertion of the delicate electrode array into the cochlear of the patient, represents major surgery, which major surgery would hopefully only need to be performed once in a patient's lifetime, it is seen that there is also a need for a fully implantable cochlear implant system wherein the battery and/or speech processor may be replaced or upgraded from time to time through minimal invasive surgery, while leaving the implantable cochlear stimulator and delicate cochlear electrode array intact for use with the replaced battery and/or upgraded speech processor.

Further, should the internal battery or speech processor within the implant system malfunction, or should the user desire not to use the internal battery or speech processor for certain time periods, there exists a need to be able to power and operate at least the stimulator portion of the implant system from an external power source so that the implant system can continue to operate and provide its intended cochlear-stimulation function until such time as a new battery and/or upgraded speech processor can be safely implanted, or for as long as desired. This affords the patient the flexibility to select when additional implant surgery, if any, is to be performed, without having to shut down operation of the existing implant system. That is, the existing implant system may thus continue to operate with the assistance of an external power boost and/or external speech processor, for as long as necessary.

SUMMARY OF THE INVENTION

The present invention addresses the above and other needs by providing a fully implantable cochlear implant system (FICIS) comprising various configurations of at least three main modules, each of which is summarized in more detail below. The three main modules include: (1) a small implantable cochlear stimulator (ICS) module, with permanently attached cochlear electrode array; (2) an implanted speech processor (ISP) module, with integrated microphone and rechargeable battery; and (3) an external module. In one embodiment, the external module may comprise an external speech processor (ESP) module. In another embodiment, the external module may comprise an external battery charger (EBC) module.

In accordance with one aspect of the invention, the small implantable cochlear stimulator (ICS) module includes the same basic cochlear-stimulation circuitry used in existing implantable cochlear stimulators, e.g., of the type disclosed in U.S. Pat. No. 5,776,172, including a permanently attached cochlear electrode array. Such circuitry is housed within a small hermetically sealed case, preferably a titanium capsule. An RF coil wraps around the exterior perimeter of the case. This coil is typically embedded within epoxy molding and connects with the circuitry inside of the case through two feed-through terminals. A two-conductor lead may, in some embodiments, also be connected in parallel with the RF coil. When used, such two-conductor lead, which may also be referred to herein as a "pigtail lead", terminates at its distal end in a plug-type jack suitable for detachable insertion into a mating connector. One side of the ICS case includes a detent, or cavity, in which a removable magnet may be housed.

In accordance with another aspect of the invention, the implantable speech processor (ISP) module is also housed within a small, hermetically sealed case. The case of the ISP module is preferably a rounded disk shape, having two internal compartments: an electronic circuitry compartment and a battery compartment. The electronic circuitry compartment houses the speech processor, microphone, battery-charging circuitry, and power transmission circuitry, The battery compartment houses a rechargeable battery. A connector assembly, housing a two-conductor connector suitable for receiving the jack from the pigtail or other lead, is formed along one segment of the perimeter edge of the housing. Suitable feed-through terminals electrically connect the two conductors of the connector assembly with circuitry housed within the hermetically-sealed electronic circuitry compartment. An edge channel groove is formed along the remainder of the perimeter edge of the housing, providing a location where the pigtail or other lead may be coiled or wrapped.

In one embodiment, one side of the case, i.e., the side proximate the electronic circuitry compartment, may be used as a microphone diaphragm, coupled to a piezo-crystal microphone mounted within the electronic circuitry compartment by a C-shaped coupling junction.

In accordance with yet another aspect of the invention, the external module may comprise a speech processor (ESP) module that includes appropriate speech processing circuitry, and a power source, e.g., a replaceable battery. Such ESP module performs essentially the same functions as are performed by the external control units used with existing cochlear stimulation systems. That is, the ESP module is capable of driving (controlling) and powering the ICS. The ESP module is further capable of performing the function of a slow battery charger, slowly recharging the battery in the ISP module.

In accordance with a further aspect of the invention, the external module may comprise a battery charger (EBC) module that includes appropriate charging circuitry for charging the battery in the ISP module. If needed, e.g., should the battery in the ISP module fail, then the EBC module could also be used as a power source for the ISP module and ICS module.

In use, the ICS module, with its cochlear electrode array, are implanted in the patient in conventional manner. To perform the implant operation, a sizeable section of skin must be folded back in order to expose the patient's skull. During the same implant surgery, the jack at the distal end of the pigtail lead from the ICS module is connected with the connector assembly on the ISP module. The ISP module may then be placed adjacent to the ICS module, with the pigtail lead being wound around and contained within the edge channel groove of the ISP module. With the ICS and ISP modules side-by-side, and with the pigtail lead being wound around the ISP module, the skin of the patient may then be folded back over the two modules, and then sutured as required in order to close the incision, completing the implant operation.

Advantageously, should it ever become necessary or desirous to replace the ISP module, e.g, for the purpose of upgrading the ISP hardware and/or replacing the ISP battery, then only a small incision, having a length that is approximately the same as the diameter of the ISP module, e.g., about 32–35 mm, need be made near where the ISP module is located, The implanted ISP module can then be removed through the small incision, rotating it as it is removed, so as to unwind the pigtail lead from the edge channel groove, much like a yo-yo. Once removed through the small incision, the jack at the distal end of the pigtail lead is detached from the connector of the removed old ISP module, and then attached to the connector of a to-be-implanted new ISP module. Once thus connected, the new ISP module is inserted back through the small incision, rotating it as it is inserted, thereby winding the pigtail lead back into the edge channel groove. The small incision may then be appropriately closed, e.g., through suturing, and the replacement implant operation is completed.

An alternative embodiment of the ICS module does not include a pigtail lead. Rather, coupling with the ISP module is achieved by way of an RF lead connected to the ISP module. A jack at one end of the RF lead allows it to be detachably inserted into the connector assembly on the ISP module, A coil at the other end of the RF lead is adapted to be positioned near, e.g., lying against, one side of the ICS module. AC signals may then be coupled between the coil at the end of the RF lead and the RF coil embedded within the case of the ICS module.

Advantageously, the present invention provides at least three main configurations that may be used by profoundly deaf patients in order to give them the sensation of hearing: (1) an ICS module used with an ESP module; (2) an ICS module used with an ISP module, recharged as needed using an EBC; or (3) an ICS module used with an ESP module, with assistance from an ESP module. Each of these three configurations is described in more detail below.

The first configuration includes an ICS module used with an ESP module, similar to existing cochlear stimulation systems. Such configuration is especially suited for small children where the head size and bone thickness cannot accommodate the whole system. The primary goal of this configuration is to upgrade it to a fully implantable system once the patient has grown sufficiently so that the head size and bone thickness are no longer a limitation.

In order to facilitate upgrading the first configuration to a fully implantable system by adding the ISP module at a later date, either of two approaches may be used for coupling the later-implanted ISP module with the previously-implanted ICS module. First, an ICS module with pigtail lead could be first implanted, with the pigtail lead not used, i.e., with the jack at the distal end of the pigtail lead not being connected to anything, but being protected with a suitable insulating protective cover or sleeve. Such unused pigtail lead may, in some instances, be wrapped around a "dummy" ISP module, which dummy ISP module would preserve a space within the pocket formed under the skin for the later-implanted actual ISP module. In small children, however, such "dummy" module would likely not be used, but rather the pigtail lead, with protective sleeve, would simply be coiled under the skin in the region where the later-implanted ISP module would eventually be located. Then, at a later date, when the ISP is implanted, the pigtail lead could be extracted through an incision, connected to a new ISP, and the ISP could then be implanted. Second, an ICS module without pigtail lead could be first implanted. Then, at a later date, when the ISP module is implanted, an RF lead could be connected to the ISP module, and the coil at its other end could be slid into position adjacent the embedded RF coil of the ICS.

The second configuration mentioned above is to use an ICS module with an ISP module, with periodic recharging from an external battery charger (EBC). Such configuration represents a fully implantable system that is self-sufficient for as long as the battery in the ISP module lasts. Typically, such battery should last, under normal use, for at least two days. The battery, of course, requires periodic recharging, which recharging may preferably occur overnight during sleep using the EBC.

The third configuration mentioned above is to use an ICS module with an ISP module with assistance from an external speech processor (ESP). The ESP is used to drive (control) the ICS and at the same time apply a slow charge to the implanted battery contained within the ISP module.

The ESP may be used in conjunction with the internal speech processor contained within the ISP module, or alternatively to take over the function of the internal speech processor should it malfunction or otherwise require replacement.

Advantageously, the above three configurations, as well as other configurations resulting from various combinations of the four modules of the invention, provide a great deal of flexibility in how the FICIS of the present invention may be used. For example, for diagnostic purposes, the ISP module may be continuously powered from the external battery charger (EBC), which itself may be a small, lightweight external unit. Thus, in the event the implanted battery within the ISP module malfunctions, or for whatever reason cannot be used, or the user or clinician (or other medical personnel) does not want to use it, it is still possible, through use of the EBC to provide operating power to the ISP module and ICS module so that they may continue to function for their intended purpose (e.g., stimulating and/or sensing). By having such a backup option available, the patient may delay indefinitely battery-replacement and/or corrective surgery.

It is thus an object of the present invention to provide a modular-based fully implantable cochlear implant system (FICIS) that is flexible in its application to meet the particular needs and wants of a given patient at a given time, including the ability to adapt to a range of head sizes and shapes.

It is an additional object of the invention to provide such a modular-based FICIS that offers a relatively simple and low-risk replacement surgery for its battery module, e.g., the ISP module.

Yet another object of the invention is to provide such a modular-based FICIS that is highly reliable, exhibiting, e.g., life-time reliability for the ICS module, cochlear electrode array, and pigtail lead (when used), and further exhibiting a reliability of the ISP module that is equal to or better than the maximum life of the battery used therein.

Still a further object of the invention is to provide a modular-based FICIS that is relatively easy to manufacture in a cost effective manner.

BRIEF DESCRIPTION OF THE DRAWINGS

The above and other aspects, features and advantages of the present invention will be more apparent from the following more particular description thereof, presented in conjunction with the following drawings wherein:

FIG. 3A depicts a top view of an FICIS made in accordance with the invention, and further illustrate the manner in which the pigtail lead originating at the ICS module is detachably connected to the connector of the ISP module, and wraps around the ISP module in the edge channel groove of the ISP module;

FIG. 3B depicts a side view of the FICIS shown in FIG. 3A, with the pigtail lead being wrapped around the ISP module;

FIGS. 6A and 6B show a side and top view, respectively, of an implanted cochlear stimulator (ICS) as in FIGS. 4A–4C, and further show one way, using a deep indentation in the shell, that electrical connection may be made with the non-hermetically sealed RF coil on the outside of the ICS shell from an hermetically-sealed location on the inside of the ICS shell;

FIG. 6C illustrates an enlarged side view of the ICS module of FIGS. 6A and 6B, with a portion of the module's walls cut away to show the construction and arrangement of internal components used within the ICS module;

4A–4C, and further show another way, using a shallow indentation in the shell in conjunction with a titanium tube, that electrical connection may be made with the non-hermetically sealed RF coil on the outside of the ICS shell from an hermetically-sealed location on the inside of the ICS shell.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Overview

The present invention relates generally to a fully implantable system having a rechargeable battery (or other power source). Such systems are described, including the rechargeable battery portion, in Applicant Faltys' copending patent application Ser. No. 09/126,615, filed Jul. 31, 1998, now U.S. Pat. No. 6,067,474, which patent is incorporated herein by reference.

A preferred embodiment of the present invention relates to an implantable cochlear stimulation system that is partitioned into two components: (1) a cochlear stimulator component and associated electrode array which are designed to last for the life of the patient; and (2) an implantable speech processor and battery component which are designed to be explanted and replaced from time to time. It is to be understood, however, that other embodiments of the invention may be used, For example, the invention may be practiced in a single implantable component which comprises a fully implantable cochlear stimulation system. It is also to be understood that the present invention need not be limited to just a cochlear stimulation system. Any medical or other device or system which must be implanted in living tissue, or a similar environment, and which requires operating power from a replenishable power source, such as a rechargeable battery, and wherein the operating power must be inductively or magnetically or otherwise coupled into the implantable device without a direct electrical connection, may benefit from the application and teachings of the present invention.

Figure 1A:
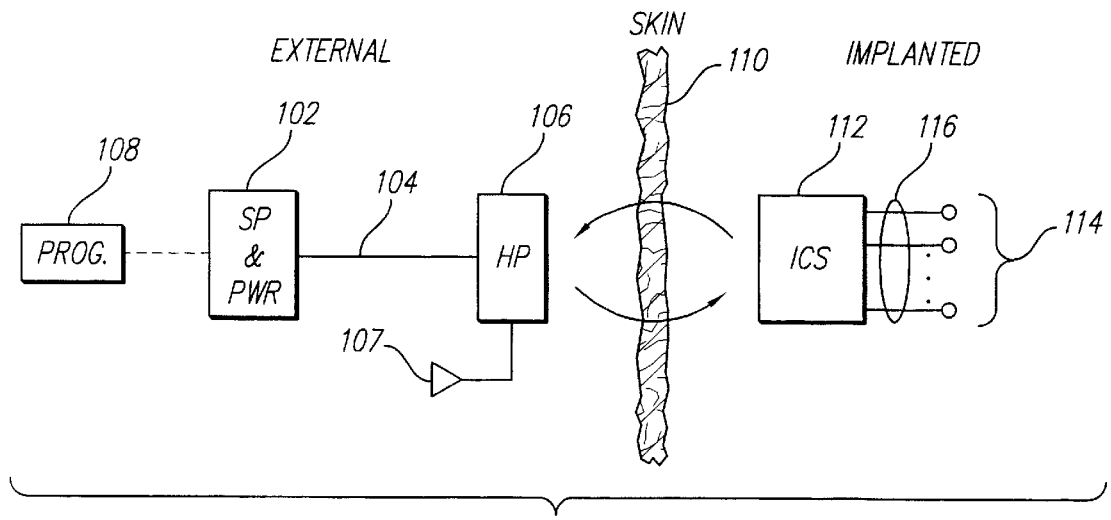
FIG. 1A illustrates a typical cochlear stimulation system as currently used by many patients, including an implantable cochlear stimulator (ICS) that is inductively coupled with an external headpiece (HP) connected with an external speech processor (SP) and power source.

To better understand and appreciate the present invention, it will be helpful to briefly review current or existing cochlear stimulation systems, which are generally representative of all tissue-stimulating systems. A representative cochlear stimulation system of the type currently used by many patients is fully described, e.g., in U.S. Pat. No. 5,776,172, previously referenced and incorporated herein by reference. As described in the '172 patent, and as illustrated in FIG. 1A, such existing system includes implanted and external components. The external components include a speech processor (SP), a power source (e.g., a replaceable battery), and a headpiece (HP) 106. The SP and power source are typically housed within a wearable unit 102 that is worn or carried by the patient. The wearable unit is electrically connected to the HP 106 via a cable 104. A microphone 107 is also included as part of the headpiece 106.

The implanted components include an implantable cochlear stimulator (ICS) 112 and an array of electrodes 114. The electrode array 114 is intended for implantation within the cochlear of the patient. The ICS 112 is implanted behind the ear, so as to reside near the scalp. The electrode array 114 is permanently connected to the ICS by way of a multi-conductor implantable cable 116.

Inside of the headpiece 106 is a coil that is used to inductively or magnetically couple a modulated ac carrier signal to a similar coil that is included within the ICS 112. In order to achieve efficient coupling, without suffering significant losses in the signal energy, it is important that the external coil within the headpiece be properly aligned with the internal coil inside the ICS. To achieve proper alignment, a magnet is typically included within both the headpiece 106 and the ICS 112, and the resulting magnetic attraction between the two magnets not only aligns the coils, as desired, but also provides a holding force that maintains the headpiece 106 securely against the scalp or skin 110 of the patient. Disadvantageously, the use of such a magnet may, for some patients, limit their ability to have magnetic resonance imaging (MRI) performed on them, at least in the vicinity of the head.

In use, a carrier signal is generated by circuitry within the wearable unit 102 using energy derived from the power source within the speech processor unit 102. Such carrier signal, which is an ac signal, is conveyed over the cable to the headpiece 106 where it is inductively coupled to the coil within the ICS 112. There it is rectified and filtered and provides a dc power source for operation of the circuitry within the ICS 112. Sounds are sensed through the external microphone 107, amplified and processed by circuitry included within the speech processor unit 102, and converted to appropriate stimulation signals in accordance with a selected speech processing strategy by circuitry within the speech processor unit 102. These stimulation signals modulate the carrier signal that transfers power to the ICS 112. The ICS includes an appropriate demodulation circuit that recovers the stimulation signals from the modulated carrier and applies them to the electrodes within the electrode array 114, The stimulation signals identify which electrodes, or electrode pairs, are to be stimulated, the sequence of stimulation and the intensity of the stimulation.

Some embodiments of the ICS 112, as indicated in the '172 patent, include a back telemetry feature that allows data signals to be transmitted from the ICS 112 to the headpiece 106, and hence to the Speech Processor 102. Such back telemetry data provides important feedback information to the speech processor regarding the operation of the ICS, including the amount of power needed by the ICS. See, e.g., copending patent application Ser. No. 08/932,565, filed Sep. 19, 1997, now U.S. Pat No. 5,876,425, issued to the same assignee as the present application, and also incorporated herein by reference.

When adjustment or fitting or other diagnostic routines need to be carried out, an external programming unit 108 is detachably connected to the SP unit 102. Through use of the external programmer 108, a clinician, or other medical personnel, is able to select the best speech processing strategy for the patient, as well as set other variables associated with the stimulation process. See, e.g., U.S. Pat. No. 5,626,629, incorporated herein by reference, for a more detailed description of a representative fitting/diagnostic process.

Although the system shown in FIG. 1A has been of great value and benefit to many patients who could not otherwise experience the sensation of hearing, there are several drawbacks associated with use of the system. For example, the wearable unit 102 must be worn or carried by the patient, and the cable 104, which may be up to one meter long, must be routed from the unit 102 to the headpiece 106. Some patients find wearing the unit 102 to be inconvenient, and find the use of the headpiece 106, with its cable 104, to be unsightly and uncomfortable.

Figure 1B:
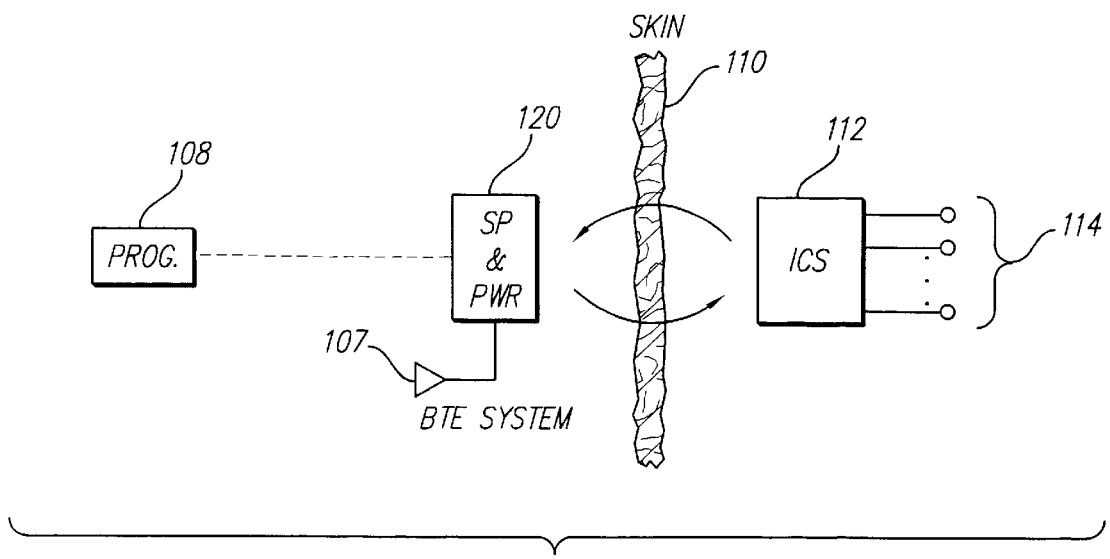
FIG. 1B illustrates a behind-the-ear (BTE) cochlear stimulation system that includes an implanted cochlear stimulator (ICS) and an external BTE unit that includes a power source, a speech processor and a microphone.

In order to eliminate the need for the cable 104, a behind-the-ear (BTE) unit 120 has been proposed, as illustrated in FIG. 1B. The BTE unit 120 may include everything that was previously included within the wearable unit 102, only in a much smaller volume. The BTE unit 120 thus includes a suitable power source, as well as the circuitry needed for performing a desired speech processing function. With the BTE unit 120, there is thus no need for the cable 104, and the patient simply wears the BTE unit behind his or her ear, where it is hardly noticed, especially if the patient has hair to cover the BTE unit.

Advantageously, the batteries employed within the wearable unit 102 (FIG. 1A) or the BTE unit 120 (FIG. 1B) may be readily replaced when needed. Still, the BTE unit 120 may become uncomfortable to wear when worn for long periods of time, and must be removed at certain times, such as when swimming or bathing. Some patients would thus like the convenience of being able to hear at all times, including when swimming or bathing, and thus a fully implantable stimulation system is desired.

The present invention is directed to fully implantable devices and systems that employ a rechargeable battery or other replenishable power source. While it is known in the art to use an implantable stimulating device with a rechargeable battery, see, e.g, U.S. Pat. No. 3,942,535, such recharging systems require a bulky external recharging system, and are time consuming to use.

In contrast, the present invention, which uses a rechargeable battery, allows the recharge operation to occur quickly and conveniently, without significant impact on the patient's lifestyle.

The present invention also allows different implant configurations to be used as part of the fully implantable system, including, in one embodiment, the ability to use the ICS 112 of the prior systems in a fully implantable system.

Figure 1C:
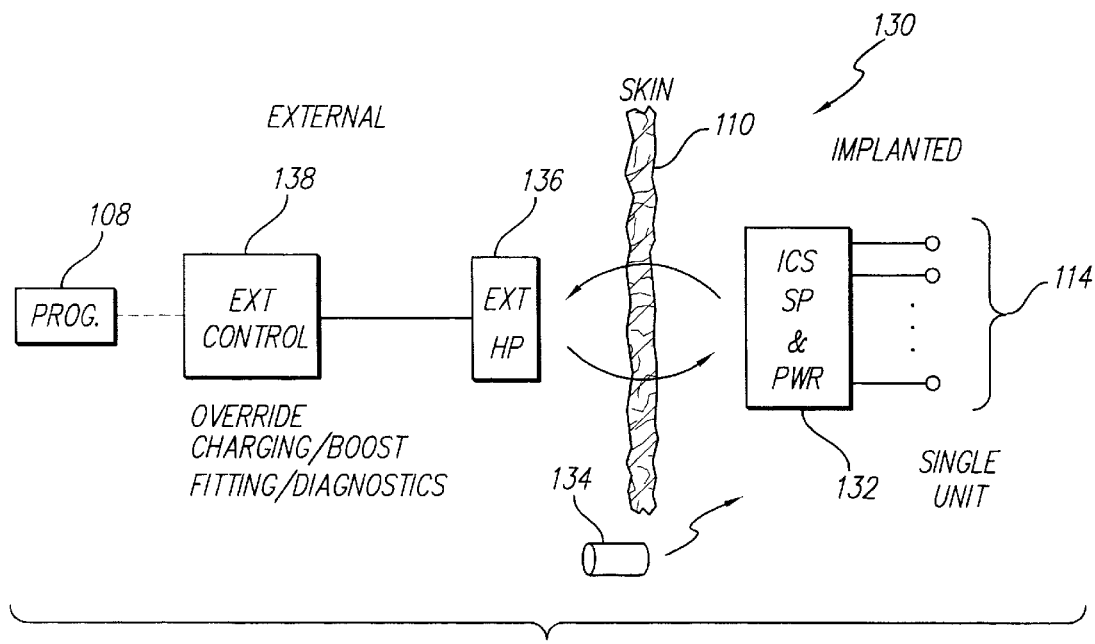
FIG. 1C shows one type of a single unit, fully implantable cochlear stimulation system.

A fully implantable single component system 130 made in accordance with the invention is shown in FIG. 1C.

As illustrated in FIG. 1C, such system 130 includes the ICS circuitry, the speech processor circuitry, and a power source within a single unit 132. An electrode array 114 is connected to the single unit 132 in conventional manner. For the embodiment shown in FIG. 1C, a microphone 134 is coupled via a telecoil link to the single unit 132. Such telecoil link powers the microphone circuits through magnetic coupling from the unit 132. Sounds sensed by the microphone 134 are transmitted to the unit 132 via an rf transmitter built-in to the microphone 134. (The transmission distance for such signal is very short, only a centimeter or two, so not much power is needed for such transmission.) Advantageously, such microphone 134 may be inserted inside the ear canal so it is not visible externally.

Other types of microphones may also be used with the implant unit 132. For example, externally-generated sound waves may be sensed through the patient's skin and case shell or wall of the single unit 132 at locations where the case shell or wall is properly supported and of the proper thickness.

When the battery included within the single unit 132 needs to be recharged, which may only be a few minutes a day, or a few times during the week, an external headpiece 136 is placed adjacent the unit 132, and inductive coupling is used to transfer charging power to the unit's battery. The external headpiece, in turn, connects to an external control unit 138, which may, in turn, derive its power from replaceable batteries or from an ac power plug. When programming and/or diagnostic tests are needed, an external programmer 108 may be detachably connected to the external control unit 138.

The external control unit 138 may thus be used to charge/recharge the battery within the implanted unit 132, as well as for other purposes. For example, the external control unit 138 may be used to override the internal speech processor with an external speech processor, e.g., a speech processor included within the external programmer 108. Further, the external control unit 138 may be used to boost the power provided by the internal battery. The external control unit 138 may also be used for programming the implant device 132, e.g., fitting the ICS after implant or adjusting the stimulation parameters of the fully implantable unit 132, as well as for diagnostic purposes.

For the embodiment 130 shown in FIG. 1C, as well as for the other embodiments shown in FIGS. 1D and 1E, discussed below, it is to be understood that back telemetry may be employed to allow data signals to be sent from the implanted unit to the external headpiece 136, and hence to the external control unit 138.

Figure 1D:
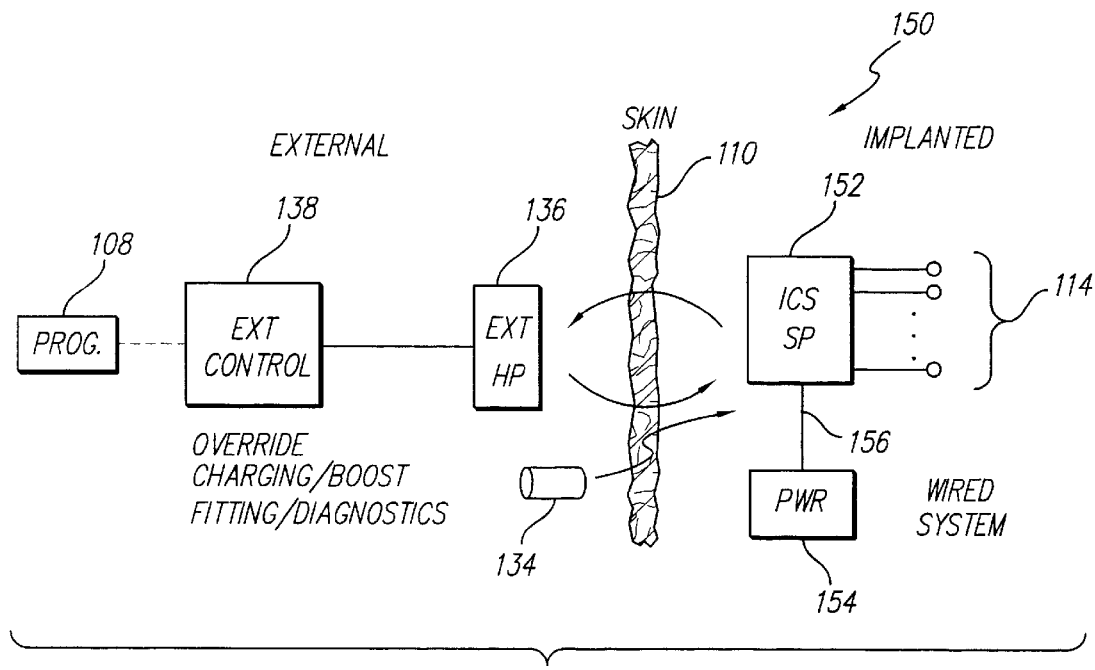
FIG. 1D shows one type of a fully implantable, partitioned, wired system in accordance with the invention.

Turning next to FIG. 1D, a "wired system" embodiment 150 of the invention is depicted. In such wired system 150, at least two separate implantable units 152 and 154 are employed and the circuits of the system are partitioned between the two units. In a first unit 152, for example, speech processor (SP) and ICS circuitry are housed, and such unit is permanently connected to an electrode array 114. In a second unit 154, a battery, or other suitable power source, is housed. The second unit 154 is electrically connected to the first unit 152 via a detachable cable 156. Other embodiments of the partitioned system may, as explained below, place the ICS circuitry in one unit, and the SP and battery in the other unit. Preferably, only ac power should be coupled from the power unit 154 to the other unit 152, thereby preventing any possibility that a dc current might flow through the tissue through which the cable is routed. This is important because a dc current could cause damage to the tissue, whereas an ac current will not. Also, because the cable is not hermetically insulated from the surrounding tissue, it is very possible that minor leakage current could flow through the tissue if it carried dc currents.

The unit 154 includes appropriate switching circuitry that converts the dc power associated with the battery (or other power storage element) therein to an ac signal for coupling to the first unit 152. Also, appropriate circuitry is employed to allow ac power induced into the unit 152 from the external headpiece 136 to be directed to the battery in the unit 154 in order to charge the battery.

Although the preferred power source for use within the fully implantable systems described herein is a rechargeable battery, it is to be understood that other power sources may also be employed. For example, an ultracapacitor (also known as a supercapacitor) may be used. An ultracapacitor, like a conventional capacitor, allows an electric charge (voltage potential) to be stored therein. Unlike a regular capacitor, the energy density of the ultracapacitor is orders of magnitude greater than the energy density of a normal capacitor, thereby allowing a great amount of energy to be stored in the ultracapacitor. This stored energy may then be withdrawn from the ultracapacitor for subsequent use. Thus, for this type of application, where recharging must occur on a regular basis, and when appropriate discharge circuits are employed to control the rate of discharge or energy withdrawal, the ultracapacitor provides a viable alternative to a rechargeable battery for use within the implantable system.

In some embodiments of the invention, a complete-in-canal (CIC) microphone 134 of the type described previously may be used to sense sounds and couple signals representative of such sounds to the speech processor (SP) circuits within its respective implantable portion.

It should be emphasized again that the partitioning illustrated in FIG. 1D, which shows that the ICS and SP circuitry are included within the first implantable unit 152, and which shows that the power source, e.g., rechargeable battery, is included within the second implantable unit 154, is only exemplary. In fact, in a preferred embodiment, described below in connection with FIGS. 2–5, the SP circuitry is included within the second implantable unit 154, leaving only the ICS circuitry within the first implantable unit 152.

The advantage of the wired system 150 shown in FIG. 1D is that a fully implantable system is provided wherein one of the two implantable units, e.g., the power unit 154, may be replaced, if necessary, through only minor surgery. As indicated, the cable 156 that connects the second unit 154 to the first unit 152 is detachable. The implantable connector that connects the cable 156 to the unit 154, may be of any suitable type, e.g., of the type commonly used with implantable pacemakers, or of the pressure type shown in U.S. Pat. No. 4,516,820 (Kuzma), incorporated. herein by reference, or of the type shown in U.S. Pat. No. 4,495,917 (Byers), also incorporated herein by reference.

The external headpiece 136 and external control unit 138, and programmer 108, may be used with the wired system embodiment 150 shown in FIG. 1D in the same manner as these components are used with the single unit embodiment 130 shown in FIG. 1C.

Figure 1E:
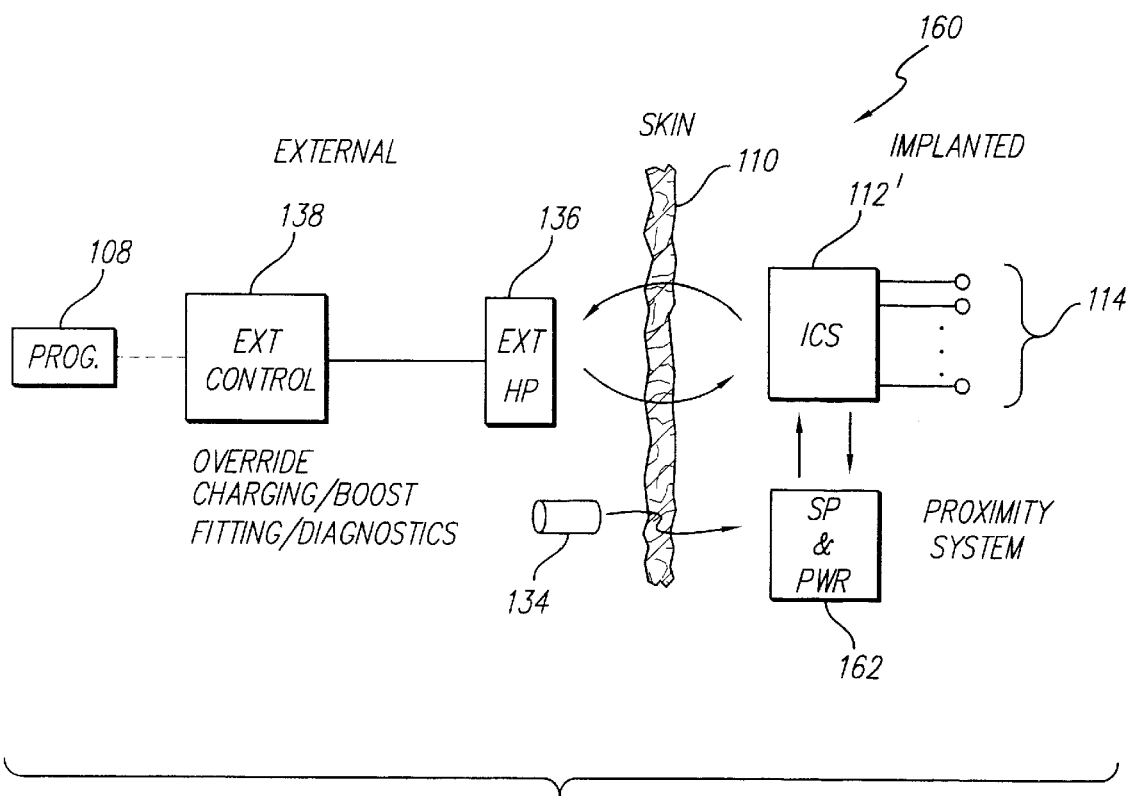
FIG. 1E shows one type of a fully implantable, partitioned, proximity system in accordance with the invention.

Turning next to FIG. 1E, a partitioned proximity system 160 is shown that is similar to the wired system 150 shown in FIG. 1D, but without the use of a connecting cable 156 connected between the two units. As seen in FIG. 1E, a first implantable unit 112' comprises an ICS with an electrode array 114 connected thereto. An advantage of the proximity system 160 is that the first implantable unit 112' may be substantially the same as, or identical to, that of the ICS 112 used in existing cochlear stimulation systems (see FIG. 1A or FIG. 1B). This allows existing stimulation systems having an ICS 112 to be upgraded to a fully implantable system as shown in FIG. 1E. A second implantable unit 162 includes speech processor (SP) circuits and a power source, e.g., a rechargeable battery. The second unit 162 is implanted so as to be in close proximity to the first unit 112'. As explained in more detail below, a preferred configuration includes a two-conductor cable or lead having one end detachably connected to the unit 162 and having a coil attached at its other end and placed or positioned against or near the first unit 112' so as to be aligned with the coil included within the first unit 112'. An edge channel grove is formed around the periphery of the second unit 162, and provides a convenient channel into which the cable or lead may be wound, like the string of a yo-yo, as the second unit 162 is positioned adjacent the first unit 112'. This allows inductive coupling to occur between the implantable units 112' and 162 in the same manner as occurs between the BTE unit 120 and the ICS 112 shown in FIG. 1B, or between the headpiece 106 and the ICS 112 shown in FIG. 1A.

A suitable microphone, e.g., an complete-in-canal (CIC) microphone 134 of the type described previously, may be used to sense sounds (pressure waves) and couple electrical signals representative of such sounds to the speech processor (SP) circuits within the implantable portion 162. Alternatively, as described below, a suitable microphone may be fashioned as an integral part of the second unit 162.

The external headpiece 136 and external control unit 138, and programmer 108, may be used with the partitioned proximity system embodiment 160 shown in FIG. 1E in the same manner as used with the single unit embodiment 130 shown in FIG. 1C and the partitioned wired system embodiment 150 shown in FIG. 1D.

By using the system shown in FIG. 1E, it is seen that the following advantages are achieved: (1) older implants, i.e., existing ICS units 112, may be upgraded to fully implantable systems without replacing the implant unit 112 and electrode 114; (2) implantable systems may be upgraded with improved battery (or other power source) technology and lower-power more-sophisticated SP circuits, as such become available, with only minor surgery for the patient; (3) batteries can be replaced with only minor surgery, as required; and (4) charging, override, power boost, fitting and diagnostics may be performed by simply overriding the implanted SP circuits with an external speech processor.

Description of a Preferred FICIS

With the foregoing as a foundation for the principles practiced by the present invention, a more complete description of a preferred fully implantable cochlear implant system (FICIS) will next be described. Three possible configurations of such a preferred FICIS are respectively illustrated in FIGS. 2A, 2B and 2C; and a functional block diagram of such a preferred FICIS is illustrated in FIG. 2D. As seen in these figures, and particularly in FIG. 2D, the FICIS comprises a modularized system that includes various combinations of at least three modules. The three modules include: (1) a small implantable cochlear stimulator (ICS) module 10, with permanently attached cochlear electrode array 12; (2) an implanted speech processor (ISP) module 30, with integrated microphone 32 and rechargeable battery 34; and (3) an external module 50. In one embodiment, the external module 50 comprises an external speech processor (ESP) module. In another embodiment, the external module 50 comprises an external battery charger (EBC) module.

At the outset it should be noted that the present invention is not directed, per se, to the specific electronic circuitry or electronic componentry used or housed within each of these four modules. Any type of suitable circuitry could be used in the modules that performs the functions indicated. Circuitry and componentry suitable for these purposes is disclosed, e.g., in the referenced patents. The present invention, rather, is directed to a system that combines the indicated modules in a way that provides the advantages and benefits enumerated herein, which advantages and benefits have not heretofore been available.

As schematically seen best in FIG. 2D, the ICS module 10 includes ICS circuitry 14 hermetically sealed in compartment 15. Electrical feed-through pins ("feedthrus") 17 and 19 connect a coil 20 to the ICS circuitry 14. The coil 20 is thus not housed within the hermetically sealed compartment 15, but is embedded within a suitable biocompatible substance 21, e.g., epoxy molding, which is affixed to the walls of the sealed compartment 15. Other feedthrus 22 electrically connect the electrode array 12 to the ICS circuitry 14 through an non-hermetic compartment 23, as explained more fully below in conjunction with FIG. 4C.

The electrode array 12 includes a multiplicity of spaced-apart electrode contacts 13 at its distal end, which electrode contacts are adapted to be placed inside of the cochlear in order to provide an electrical stimulus to the tissue within the cochlear. A typical electrode array 12 may include, e.g., anywhere from 8 to 22 electrode contacts 13.

In addition to the coil 20 which is connected to the feedthrus 17 and 19, one embodiment of the present invention utilizes a two-conductor lead 18 that is electrically connected in parallel with the coil 20. That is, one of the conductors of the lead 18, which may hereafter be referred to as a "pigtail" lead, is electrically connected to the feedthru 17, and the other of the conductors of the lead 18 is electrically connected to the feedthru 19. A jack 25, including, e.g., a tip electrode 24 (connected through one of the conductors of the lead 18 to the feedthru 17) and a ring electrode 26 (connected through the other of the conductors of the lead 18 to the feedthru 19), or other suitable electrode contacts, are located at a distal end of the lead 18.

Still referring to FIG. 2D, it is seen that the ISP module 30 includes an hermetically sealed compartment 31 wherein ISP and other electronic circuitry 33 (hereafter "ISP circuitry" 33) is housed, along with a piezo-microphone 32 and a rechargeable battery 34. Feedthrus 35 and 37 electrically connect the ISP circuitry 33 to an electrical connector 36 formed in a suitable biocompatible material, e.g., epoxy molding, affixed to one side or edge of the ISP module 30. Advantageously, the jack 25 at the distal end of the lead 18 may be detachably inserted into the connector 36. When thus inserted, the tip electrode 24 makes electrical contact through feedthru 35 with the ISP circuitry 33, and the ring electrode 26 makes electrical contact through feedthru 37 with the ISP circuitry 33. Those of skill in the art will readily recognize that this type of connector is similar to the basic connectors used in the pacemaker art in order to detachably connect a pacing lead to an implanted pacemaker. See, e.g., U.S. Pat. No. 4,764,132 (Stutz, Jr.) and the art cited therein.

One embodiment of the present invention includes the use of an RF lead 18' in place of the pigtail lead 18. As seen in FIG. 2D, the RF lead 18' has a jack 25' at one end having a tip electrode 24' and a ring electrode 26', adapted for insertion into the connector 36 of the ISP module 30. At the other end of the lead 18' is an RF coil 20'. When used, the coil 20' of the RF lead 18' is positioned as close as possible to, and in alignment with, the coil 20 embedded within the molded epoxy 21 of the ICS module 10.

As seen in FIG. 2D, both the ICS module 10 and the ISP module 30 are adapted to be implanted beneath the skin layer 110 of the patient. When the battery 34 has sufficient charge stored therein, the operation of the ICS module 10 and ISP module 30 proceeds without assistance from any external components. Thus, the system created by the ICS module 10 and ISP module 30 is self-sufficient, and truly becomes a fully implantable cochlear implant system that provides the patient with the sensation of hearing.

As needed, the fully implantable system may be assisted or boosted with an external module 50. Such external module 50 may be needed, e.g., to charge the battery 34, or to override the ISP circuitry 33 with external speech processing controls and commands. Such external module 50 includes a headpiece 50', having a coil 52 therein. In some embodiments, the headpiece 50' may also include an external microphone. The headpiece 50' is connected to an external unit 54, which external unit comprises appropriate electronic circuitry, e.g, an external speech process (ESP) or an external battery charger (EBC). The external unit 54, in turn, is powered from an external power source 56. Typically, the external power source will comprise a replaceable battery. However, the external power source could conceivably be any available power source, including batteries, including either replaceable or rechargeable batteries; charged super capacitors; dc power supplies connected to the ac line voltage (110 vac, 60 Hz); solar panels; hand-operated generators; or the like.

Figure 2A:
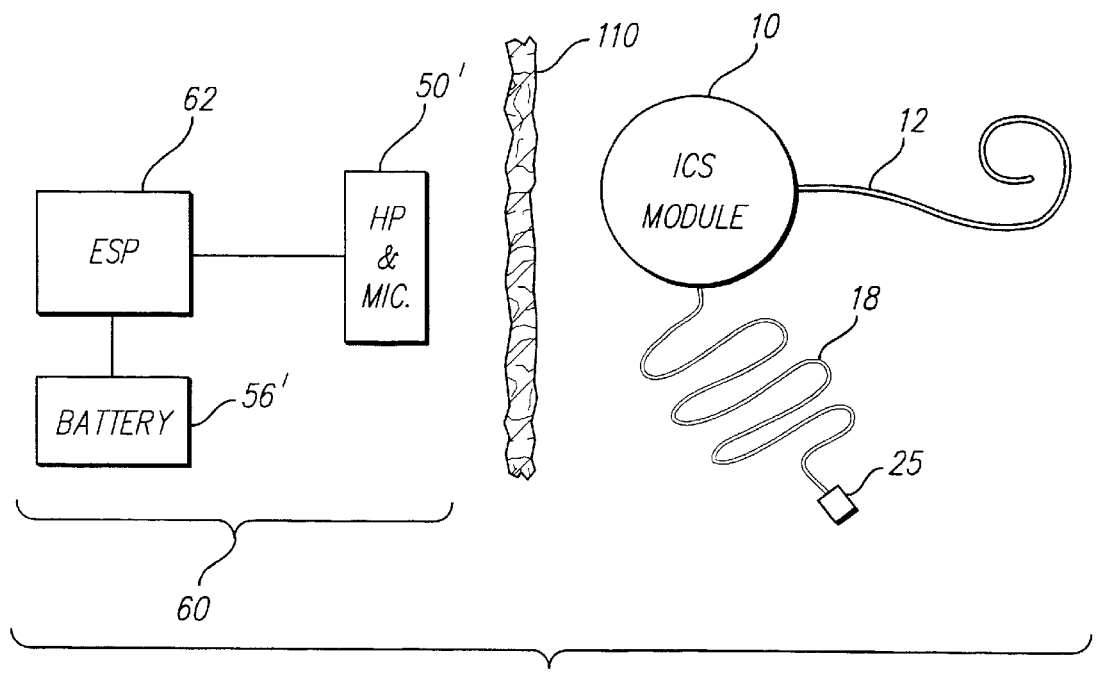
FIGS. 2A, 2B and 2C illustrate, respectively, three different configurations that may be realized using modularized fully implantable cochlear implant system (FICIS) in accordance with the present invention.

FIG. 2A illustrates one variation of the invention that is particularly well suited for young children. This variation includes an ICS module 10 used with an ESP module 60. The ESP module 60 includes a headpiece and microphone 50', an external speech processor 62 and related circuitry, powered by a battery 56'. As such, the variation shown in FIG. 2A is similar to existing cochlear stimulation systems (see, e.g., FIG. 1A). The configuration shown in FIG. 2A is especially suited for small children where the head size and bone thickness cannot accommodate the entire FICIS system. The primary goal of this configuration is to upgrade it to a fully implantable system once the patient has grown sufficiently so that the head size and bone thickness are no longer a limitation.

The advantage of the variation shown in FIG. 2A is that in can readily be upgraded to a fully implantable system at a later date by adding an ISP module 30. The ISP module 30 may be added using either of two approaches. In a first approach, an ICS module 10 with pigtail lead 18 is first implanted, with the pigtail lead 18 not being used, as shown in FIG. 2A. That is, the jack 25 at the distill end of the pigtail lead 18 is not connected to anything when the ICS module 10 is first implanted. Typically, the jack 25 will be protected with a suitable insulating protective cover or sleeve. Such unused pigtail lead 18 may, in some instances, be wrapped around a "dummy" ISP module, which dummy ISP module would preserve a space within the pocket formed under the skin for the later-implanted real ISP module 30. In small children, however, such "dummy" module would likely not be used, but rather the pigtail lead 18, with protective sleeve, would simply be coiled under the skin in the region where the later-implanted ISP module would eventually be located. Then, at a later date, when the ISP module 30 is implanted, the pigtail lead 18 may be be extracted through an incision, connected to a new ISP module 30, and the ISP module 30 could then be implanted, coiling the pigtail lead 18 around it, as described below.

In a second approach, the ICS module 10, with or without a pigtail lead, is implanted first. Then, at a later date, when the ISP module 30 is to be implanted, an incision is made next to the ICS module 10 and a pocket is formed under the skin. An RF lead 18' is connected to the ISP module 30 by way of the connector 36. The coil 26 at the other end of the RF lead 18' is pushed into the pocket and positioned adjacent to and aligned with the embedded RF coil 20 of the ICS module 10. The ISP module 30 is then inserted into the pocket with a rotation movement so as to wind the lead 18' around the edge of the module as it is inserted. An edge channel grove is provided around the periphery of the ISP module 30 to facilitate this process. The incision that opens into the pocket is then closed with appropriate suturing or other means.

Figure 2B:
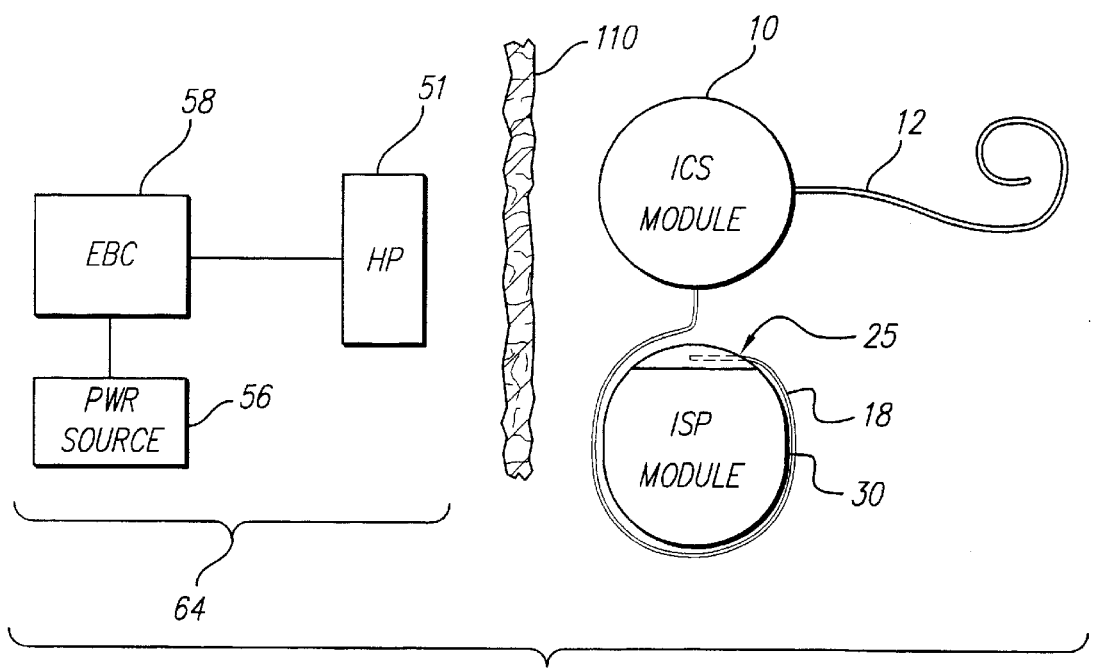

As seen in FIG. 2B, a second configuration of the invention uses an ICS module 10 with an ISP module 30. Periodic recharging of the battery 34 within the ISP module is performed using an external module 64 that includes a headpiece 51, an external battery charger (EBC) 58, and an external power source 56. The configuration shown in FIG. 2B represents a fully implantable system that is self-sufficient for as long as the battery 34 in the ISP module remains charged. Typically, such battery 34 should last, under normal use, for at least two days. The battery 34, of course, requires periodic recharging, which recharging may preferably occur overnight during sleep using the EBC 58 and related components.

Figure 2C:
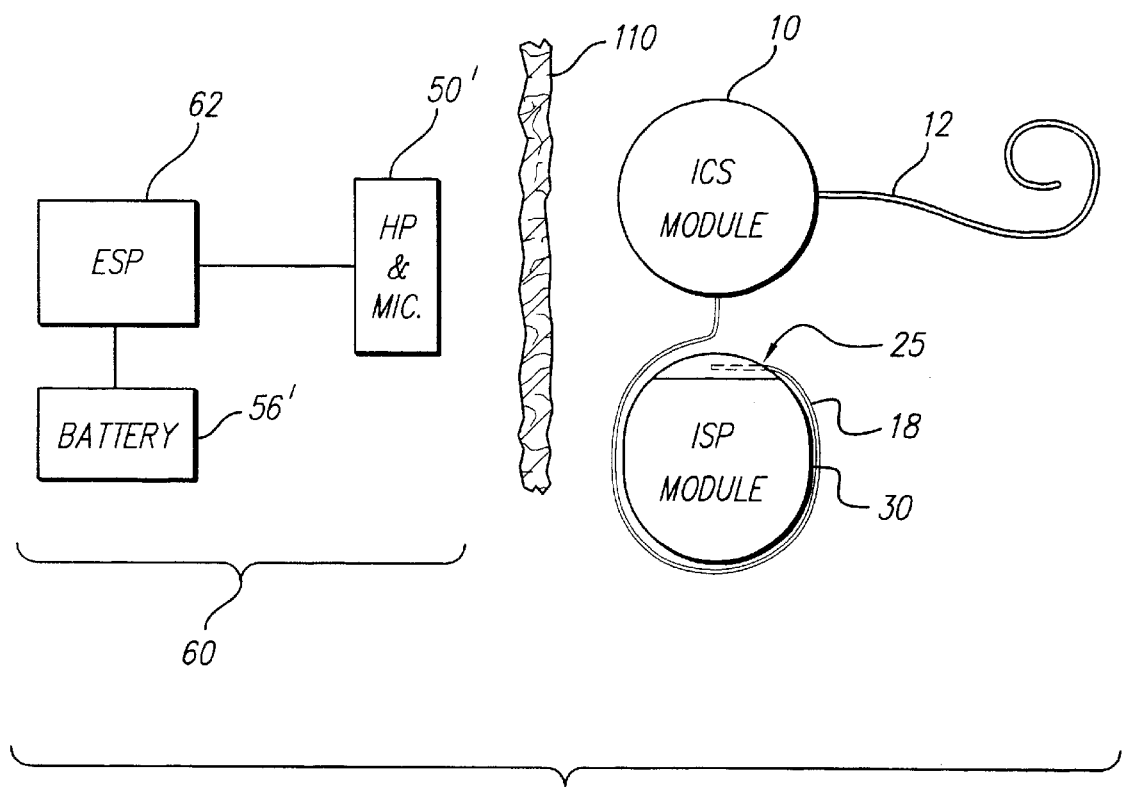
Figure 2D:
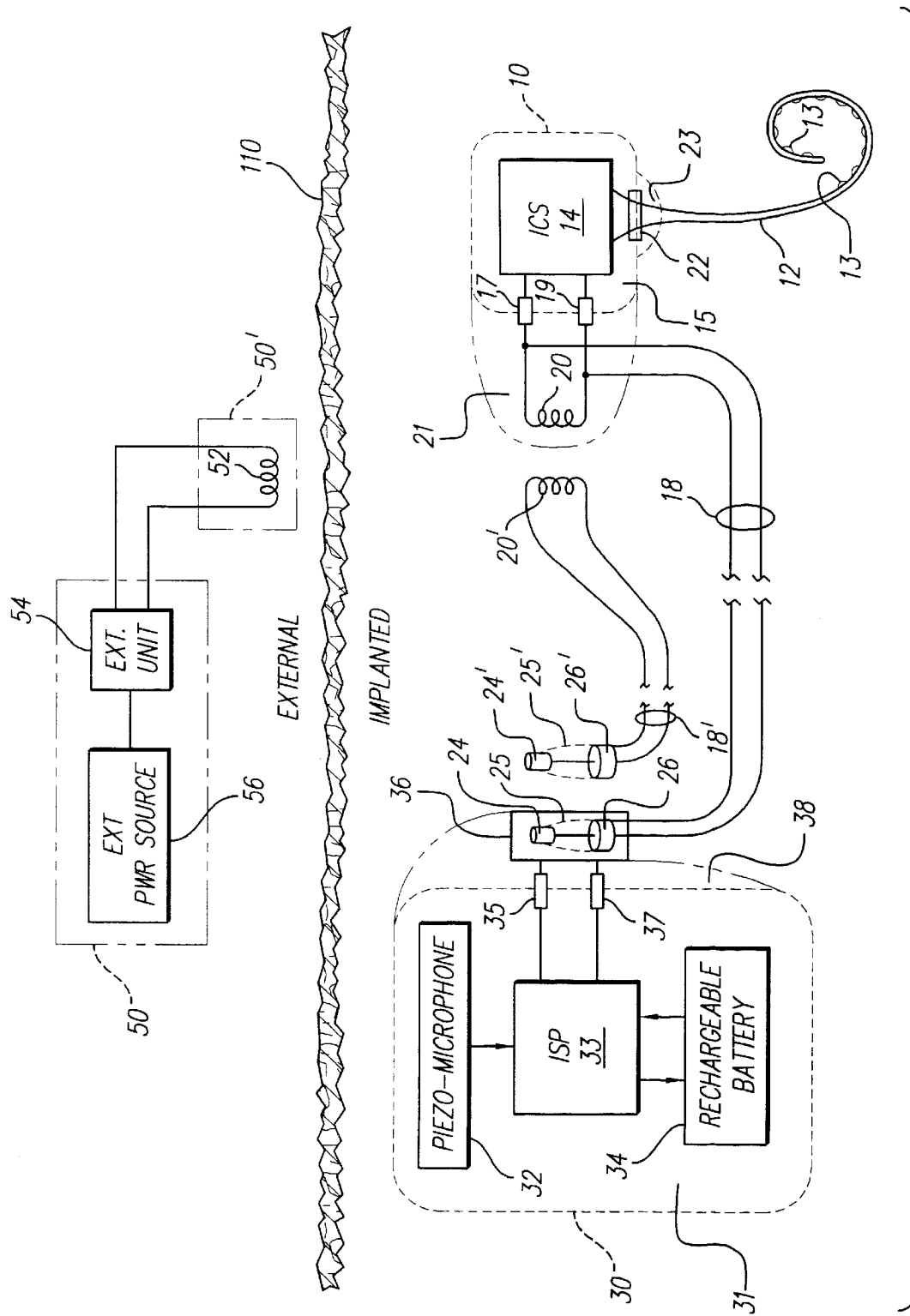
FIG. 2D is a schematic block diagram of a preferred FICIS in accordance with the invention.

Turning next to FIG. 2C, a third configuration of the invention uses an ICS module 10 with an ISP module 30 with assistance from an external speech processor (ESP) module 60. The ESP module 60 is essentially the same as that described above in connection with FIG. 2A. Such module 60 is used to drive (control) the ICS module 10 and at the same time apply a slow charge to the implanted battery 34 contained within the ISP module 30. The ESP module 60 may be used jointly with the internal speech processor 33 contained within the ISP module 30, or alternatively to take over the function of the internal speech processor should it malfunction or otherwise require replacement.

Turning next to FIGS. 3A and 3B, a top and side view, respectively, of an FICIS made in accordance with the invention is shown. These figures illustrate how the pigtail lead 18, originating at the ICS module 10, may be detachably connected to the connector 36 of the ISP module when the lead 18 is fully extended. Then, once connected, the ISP module 30 is rotated (e.g., clockwise as shown in FIG. 3A), causing the lead 18 to wrap around an edge channel groove 39 of the ISP module. This rotation causes the ISP module to pull up close to the ICS module 10, much like a yo-yo climbing a string. Having the ISP module adjacent the ICS module 10 is the desired position for the two modules when implanted.

Figure 3C:
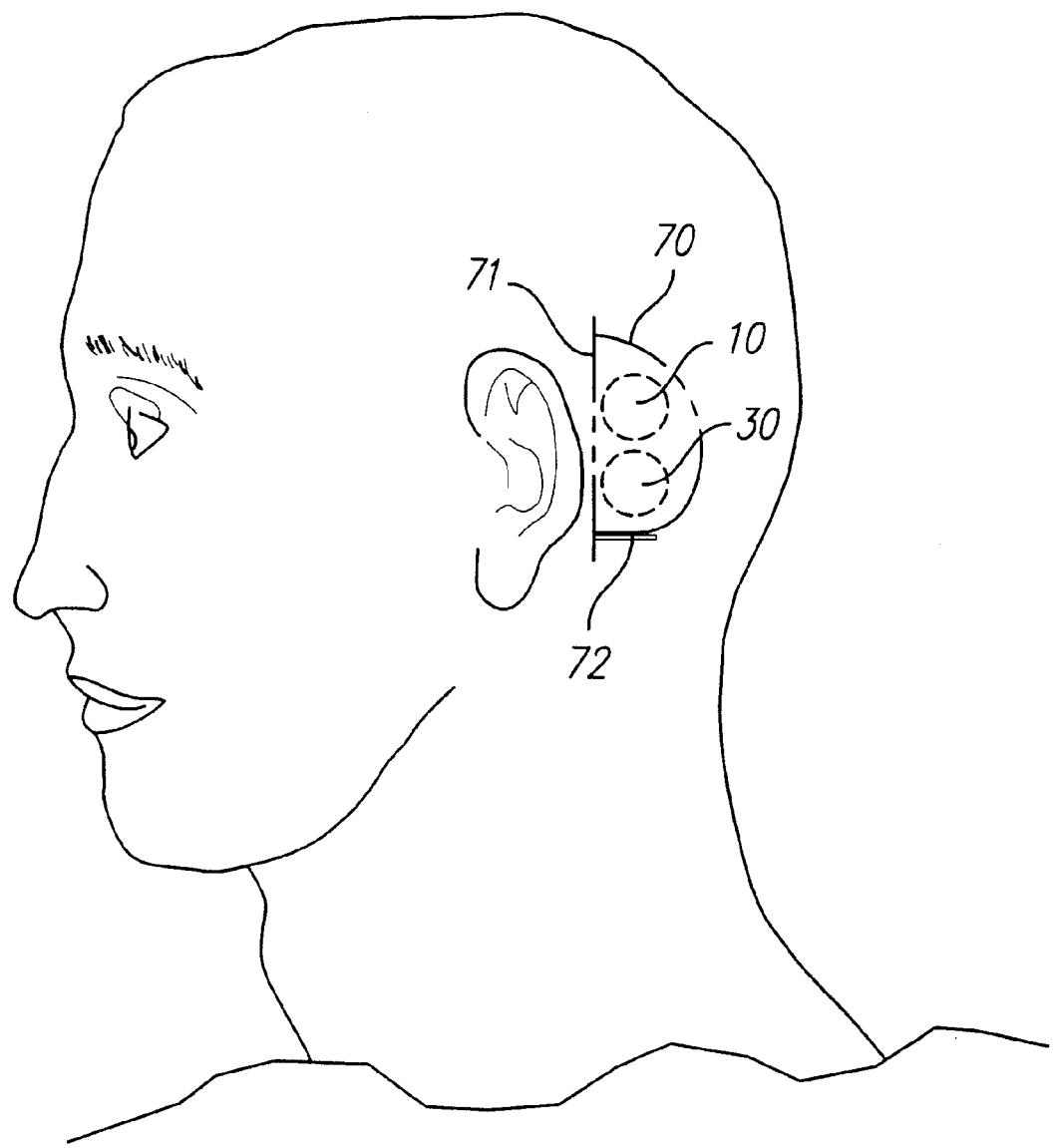
FIG. 3C diagrammatically illustrates the incisions which must be made to initially implant the FICIS and to subsequently explant the ISP module and replace it with a new one.

The significance of the yo-yo action achieved between the ICS module 10 and the ISP module 30—which yo yo actions greatly facilitates replacement surgery—becomes more apparent when one considers the process used to implant the FICIS. During an initial implant surgery, a fairly large incision 70, typically in a semi-circle pattern, must be made in the skin of the patient's head behind the ear, as depicted in FIG. 3C. The skin thus incised is folded back over the line 71 to expose the skull bone and provide an relatively large area where the ICS module 10 and ISP module 30 may be implanted. Once both modules are in place, and the cochlear electrode array 12 has been inserted into the cochlear, the skin is folded over the modules, and the incision is closed using suturing or clamps.

When replacement of the ISP module 30 is required, e.g., to replace the battery 34 (which would typically not be needed for several years), then all the surgeon need do is make a relatively small incision 72, having a length approximately equal to the diameter of the ISP module. Once the relatively short incision 72 has been made, the ISP module 30 is grabbed, e.g., with the surgeon's fingers of a forceps tool, and carefully removed from the pocket, rotating it in the appropriate direction as it is removed. As it is removed, the lead 18 thus unwinds until, when fully removed from the pocket, the lead 18 is straight and can be easily detached from the connector 36. Once detached, the jack 25 at the end of the lead 18 is cleaned, as required, and inserted into the connector 36 if a new ISP module 30. The new ISP module 30 is then inserted back into the pocket, through the incision 72, rotating it as it is so inserted, so that the lead 18 once again wraps around the edge channel grove 39 of the ISP module 30. Once inserted back into the pocket through the incision 72, the incision 72 is closed in conventional manner.

The above replacement process advantageously allows an old ISP module 30 to be explanted, the lead 18 to be disconnected from the old ISP module, the lead 18 connected to a new ISP module, and the new ISP module with lead 18 attached to be implanted, all using a relatively simple surgery, without disturbing the implanted ICS module, and its cochlear electrode array. Such surgery can, in most instances, be performed on an outpatient basis, without the necessity and expense of using a hospital operating room.

Figure 4A:
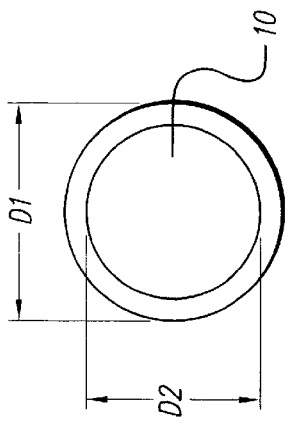
FIGS. 4A and 4B show a side and top view, respectively, of an implanted cochlear stimulator (ICS) module made in accordance with the invention.
Figure 4B:
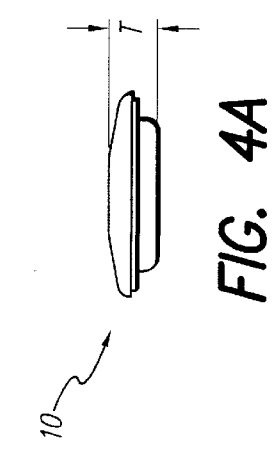

Turning next to FIGS. 4A and 4B, a side and top view, respectively, of an implanted cochlear stimulator (ICS) module 10 made in accordance with a preferred embodiment of the invention is illustrated. For clarity, the cochlear electrode lead 12 and the pigtail lead 18 have been omitted. As seen in these figures, the module 10 is preferably circular in shape, having an outer diameter D1, where D1 is about 25 mm, and an inner (cavity) diameter D2, whre D2 is about 20 mm. The thickness T of the module 10 is about 5 mm. Thus, the ICS module 10 has the general appearance of a large button.

Figure 4C:
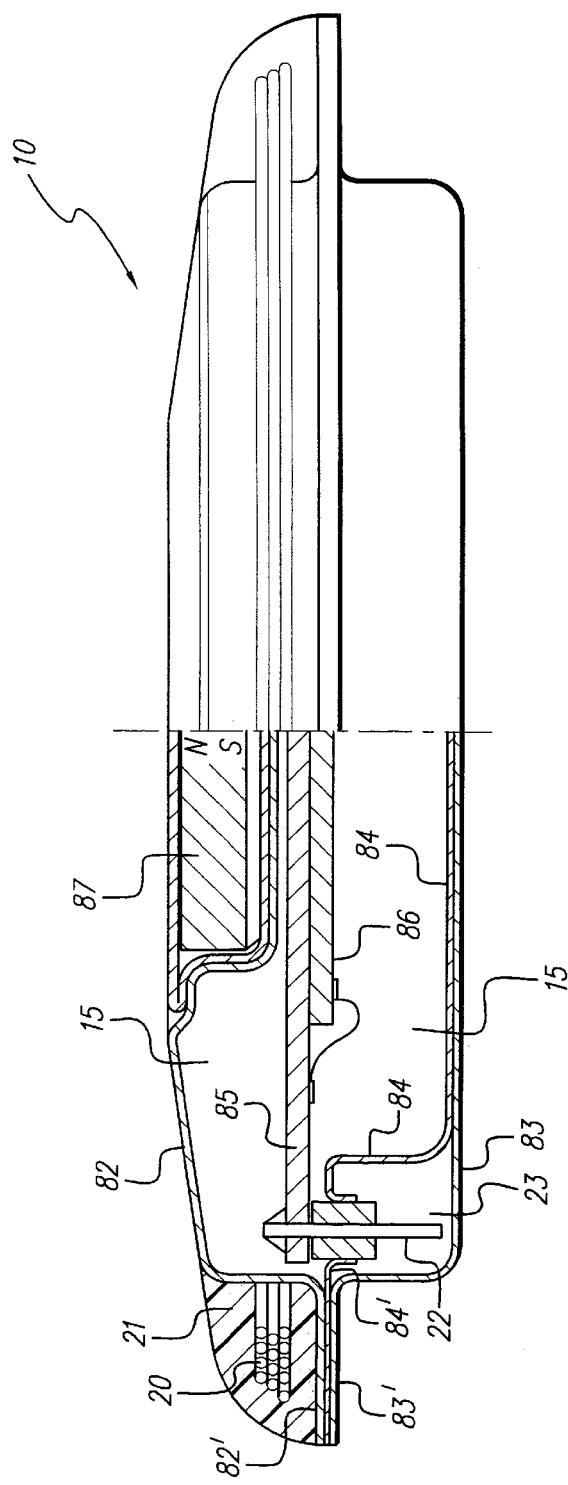
FIG. 4C illustrates an enlarged side view of the ICS module of FIGS. 4A and 4B, with a portion of the modules walls cut away to show the construction and arrangement of internal components used within the ICS module.

FIG. 4C illustrates an enlarged side view of the ICS module of FIGS. 4A and 4B, with a portion of the walls of the module cut away to show the preferred construction and arrangement of the internal components used therewithin. As seen in FIG. 4C, the preferred construction is a clam-shell construction, wherein a top shell 82, having an outwardly protruding flange 82' around its periphery, and a bottom shell 83, also having an outwardly protruding flange 83', are bonded together at the flanges by welding the flanges together. An inner shell 84, having a smaller diameter than the lower shell 83, and also having an outwardly protruding flange 84', fits inside of the lower shell 84. The flange 84' is bonded to the flanges 82' and 83' by being sandwiched between the flanges 82' and 83' as the weld is made. In this manner, all three flanges 82', 83' and 84' are welded together. All three shells 82, 83 and 84 are preferably made from titanium alloy 6AL/4D.

The space inside of the shells 84 and 82 represents an hermetically sealed cavity 15 wherein electronic circuitry, e.g., an integrated circuit 86, may be mounted on a printed circuit board (PCB) 85. Feedthrus 20, as well as feedthrus 17 and 19 (see FIG. 2D) are spaced around the periphery of the PCB 85 and pass through the flange 84' of the inner shell 84 to the space 23 inside the lower shell 83 and outside the inner shell 84. Such space 23 thus represents a non-hermetically sealed compartment that encircles the module 10 just inside of the lower shell 83 around its periphery. The existence of such ring-shaped non-hermetic compartment 23 facilitates electrical connection of the non-hermetically sealed portion of the feedthrus with the appropriate lead or coil. Once all the electrical connections have been made inside of the non-hermetic compartment 23, such compartment may be injected with a suitable dielectric filler material, e.g., a biocompatible epoxy or silicone.

The coil 20 used by the ICS module 10 is preferably embedded within a suitable biocompatible epoxy molding material 21 positioned on top of the flange 82'. The ends of the wire from which the coil 20 is made must be electrically connected with electrical circuitry located inside of the hermetically-sealed compartment. Several approaches may be used to make such connection. For example, the ends of the wires from the coil 20 may pass through the welded flange 82'/83'/84', e.g., through one or more holes, and similarly pass through one or more holes in the shell 83 into the non-hermetic compartment 23, where they may be connected to the feedthrus 17 and 19.

More particularly, one way to connect the ends of the wires from the coil 20 with electronic circuitry inside of the hermetically-sealed portions of the ICS module 10 is to use a deep indentation 102 in the upper shell 82, as illustrated in FIGS. 6A, 6B and 6C. Such deep indentation 102 provides an opening or channel to a lower surface 104 through which a hole 105 or 106 can be made into the non10 hermetically sealed cavity 23. Thus, as seen best in FIG. 4C, one end 108 of the wire from the coil 20 passes through opening 106 into the non-hermetically sealed cavity 23, where it is attached to feedthru 19. In the region around the opening 106, the shells 82 and 84 must remain hermetically sealed to each other. In a similar fashion, the other end of the wire from coil 20 may pass through another opening 105 at the bottom 104 of the indent 102 into the non-hermetically sealed cavity 23, where it may be attached to feedthru 17 (see FIG. 2D).

Figure 7A:
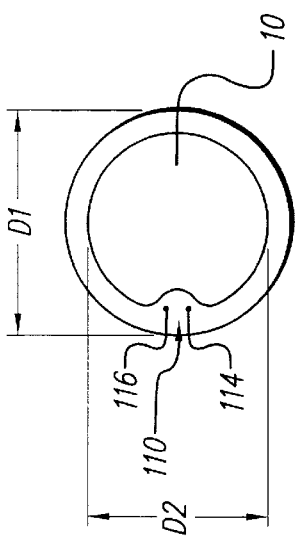
FIGS. 7A and 7B show a side and top view, respectively, of an implanted cochlear stimulator (ICS) as in FIGS.
Figure 7B:
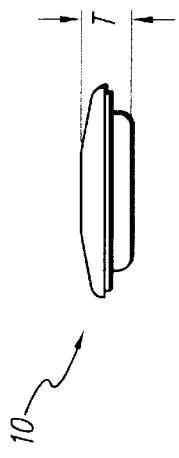
Figure 7C:
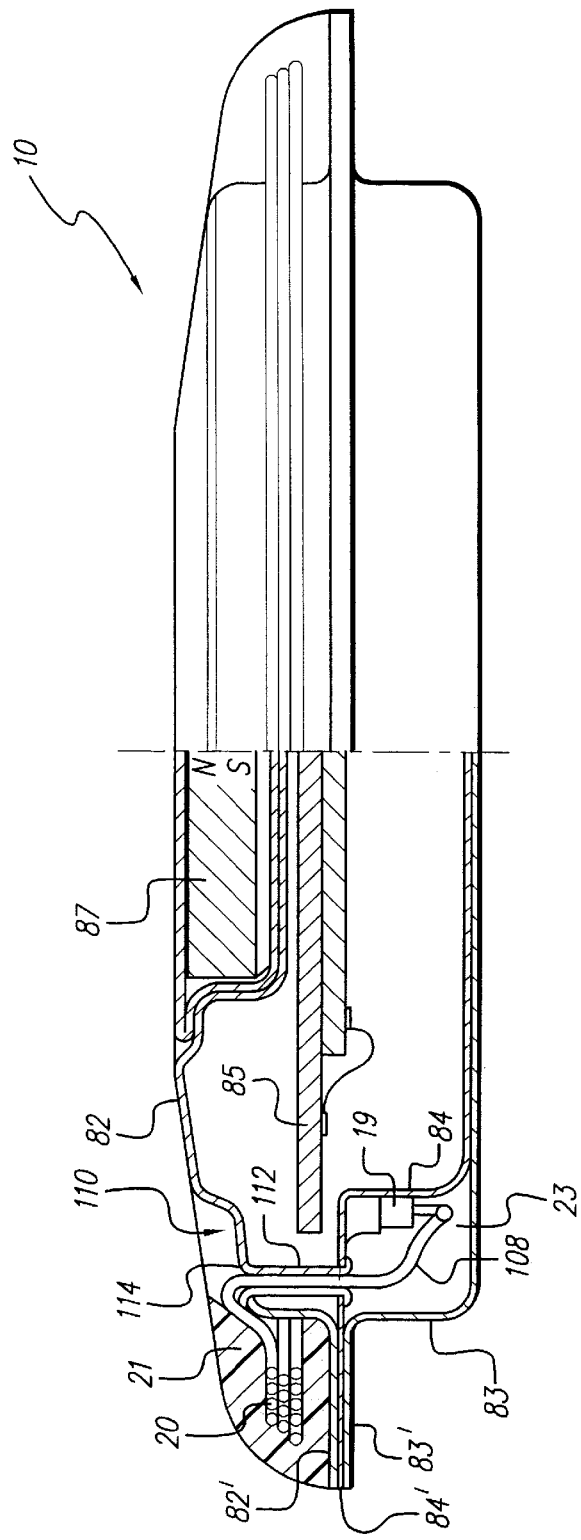
FIG. 7C illustrates an enlarged side view of the ICS module of FIGS. 7A and 7B, with a portion of the module's walls cut away to show the construction and arrangement of internal components used within the ICS module.

Another way to connect the ends of the wires from the coil 20 with the electronic circuitry inside of the hermetically-sealed portions of the ICS module 10 is to use a shallow indentation 110 in the upper shell 82 and a titanium (or titanium alloy) tube 112 as depicted in FIGS. 7A, 7B and 7C. The tube 112 is hermetically sealed with shells 82 and 84 on both ends. The wire end 108 may thus be fed through an upper end 114 of the tube 112 and passed into the non-hermetical compartment 23, where it can be attached to the feedthru 19. In a similar manner, another tube, having an upper end 116, may be hermetically sealed with shells 82 and 84 so that the other end of the wire from which coil 20 is made may pass through it into the non-hermetically sealed cavity 23.

Alternatively, with respect to the techniques shown in FIGS. 6A–6C and 7A–7C, it should also be noted that the two wire ends from the coil 20 may pass through the same opening or tube into the non-hermetically sealed cavity.

Advantageously, by spacing the feedthrus around the periphery of the PCB 35, see FIG. 4C, the manufacture and connection of a large number of conductors, e.g., as is required within the cochlear electrode array 12, is greatly facilitated. It should be noted that the cochlear electrode array 12 may pass directly through an opening in the outer shell 83 into the non-hermetic cavity 23, where each of the conductor wires used in such electrode array may connect with respective feedthrus 22 (see FIG. 2D).

In a preferred embodiment, a centrally located cavity or detent is formed within the upper shell 82. Such detent provides a cavity wherein a permanent magnet 87 may be removably inserted. Advantageously, such magnet 87 facilitates proper alignment of the coil 20 with an external coil within a headpiece, when an external unit 50 is used. Disadvantageously, such magnet 87 may interfere with needed medical resonance imaging (MRI), should such imaging be necessary in the vicinity of the skull. By making the magnet removable, the patient may thus elect not to use a magnet at the outset of the cochlear implant surgery; or, in the event MRI is subsequently indicated for the patient, the magnet may be surgically removed by making a small incision above the ICS module and pulling the magnet out, while leaving the ICS module 10 intact so that it can perform its intended function.

Figure 5B:
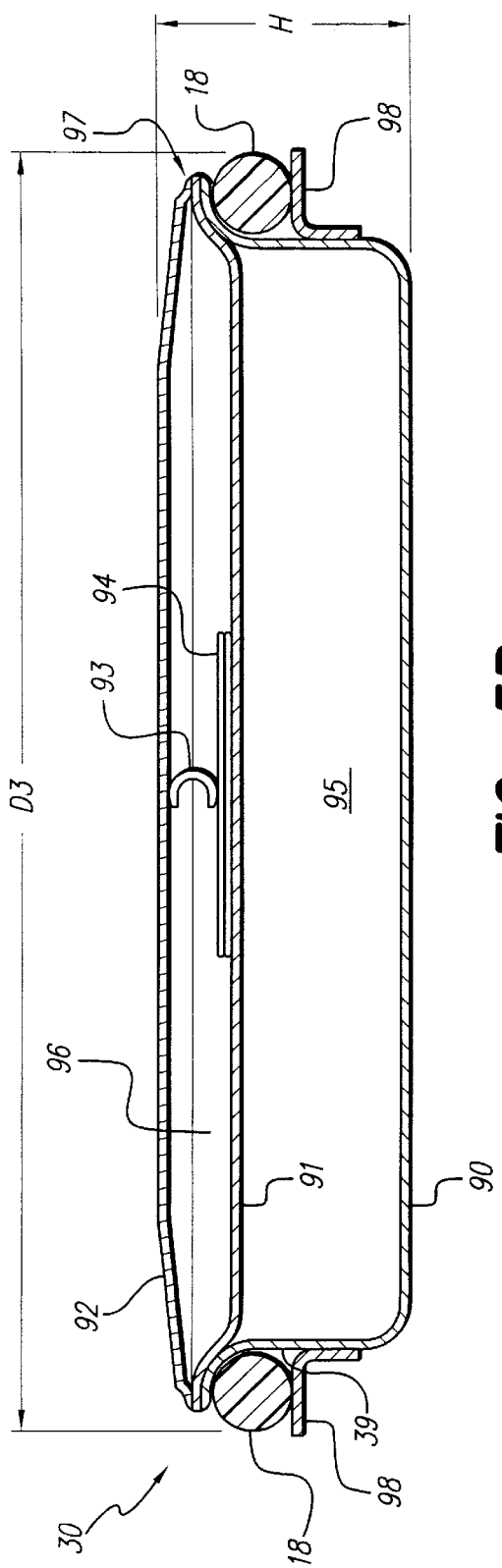
FIG. 5B illustrates a side view of the ISP module of FIG. 5A, and further depicts one type of internal microphone that may be used therein, as well as the edge channel groove for holding the wrapped pigtail lead.
Figure 5A:
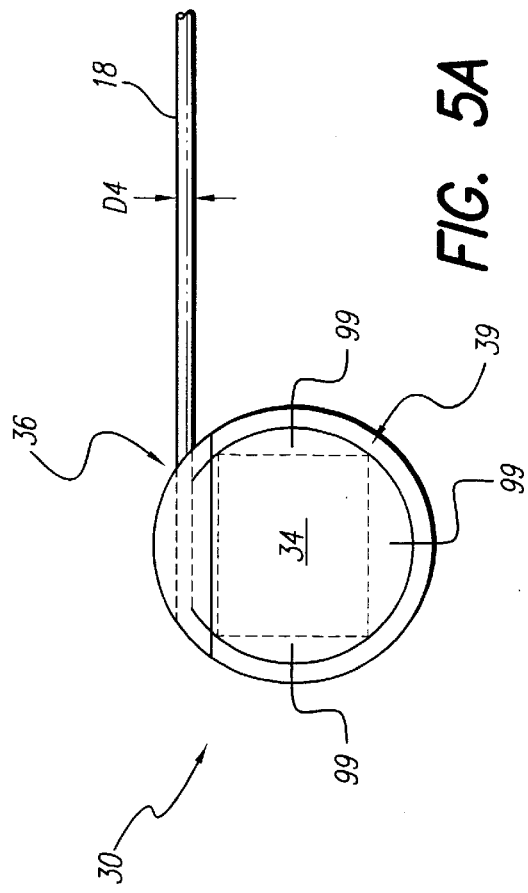
FIG. 5A shows a top view of an ISP module made in accordance with the invention, with a pigtail lead attached thereto.

FIGS. 5A and 5B show a top and side view, respectively, of a preferred ISP module 30. Like the ICS module 10, the ISP module 30 is preferably made from titanium alloy 6AL/4D, a well-proven material for use in implantable devices. The module 30 is generally circular in shape, typically having an approximate diameter D3, where D3 is about 32 mm, and a thickness, or height H, where H is about 6 mm. The pigtail lead 18, which is a two-conductor lead, has a diameter D4, where D4 is about 2 mm.

As seen best in FIG. 5B, three titanium shells 90, 91 and 92 are used to split the module 30 into two compartments: a battery compartment 95 and an electronic compartment 96. The shell 90 comprises a lower shell and has side walls approximately equal to the height of the module. The shell 91 functions as an inverted (concave) lid for the shell 90. The shell 92 functions as a lid (convex) for the shell 91. Such arrangement thus creates a lower battery compartment 95 that represents about ¾ of the available volume within the module, and an upper electronic compartment that represents about ¼ of the available volume.

Each shell includes peripheral flanges that contact each other around an upper periphery rim 97. This rim 97 provides a convenient location where a weld can be made to hermetically seal the entire unit, including both compartments. The connector 36, into which the jack 25 of the pigtail lead is detachably inserted, is formed along one segment of the perimeter of the module 30. Such connector is formed, e.g., using the same techniques and materials as have been used for years in making pacemaker connectors.

As further seen in FIG. 5B, an L-shaped flange bracket 98 is welded around the perimeter of the module 30. The flange bracket 98, in combination with the periphery rim 97, create the edge channel groove 39 into which the pigtail coil 18 is wound when the ISP module 30 is implanted next to the ICS module 10, as explained previously.

Still with reference to FIG. 5B, it is seen that a microphone is created using the upper shell 92, in combination with a coupling junction element 93 and a piezo-crystal microphone 94. Sound (pressure) vibrations pass through the skin 110 of patient and impinge on the upper shell 92. Such pressure waves are then coupled through the coupling junction 93 to the piezo-crystal microphone 94. The piezo-crystal microphone 94 responds to such pressure waves by generating an electrical signal that varies as a function of the sensed pressure waves, as is known in the art.

Other types of microphones may also be used in conjunction with, or in lieu of, the piezo-crystal microphone 94 shown in FIG. 5B. For example, as explained previously, a CIC microphone may be used to provide another source of audio signals for processing by the implantable speech processor.

As seen in FIG. 5A, the battery 34 typically has a rectangular form factor that fits within the battery compartment 95. Empty regions 99 created by the mismatch between the rectangular form factor of the battery 34 and the round shape of the module 30 may be used, as needed, to house some of the larger electronic components, e.g., capacitors, used with the ISP circuitry.

As described above, it is thus seen that the present invention provides a modular-based fully implantable cochlear implant system (FICIS). Such system advantageously is flexible in its application so as to meet the particular needs and wants of a given patient at a given time, including the ability to adapt to a range of head sizes and shapes.

As further described above, it is also seen that the invention provides such a modular-based FICIS that offers a relatively simple and low-risk replacement surgery for its battery module, e.g., the ISP module.

As additionally evident from the description above, it is seen that the invention provides such a modular-based FICIS that is highly reliable, exhibiting, e.g., life-time reliability for the ICS module, cochlear electrode array, and pigtail lead (when used), and further exhibiting a reliability of the ISP module that is equal to or better than the maximum life of the battery used therein.

While the invention herein disclosed has been described by means of specific embodiments and applications thereof, numerous modifications and variations could be made thereto by those skilled in the art without departing from the scope of the invention set forth in the claims.

What is claimed is:

1. A fully implantable cochlear implant system (FICIS) comprising:

an implantable cochlear stimulator (ICS) module having an electrode array attached thereto, the electrode array having a multiplicity of spaced-apart electrode contacts at or near a distal end thereof, each electrode contact having a respective electrical conductor attached thereto, all of the electrical conductors being electrically connected with stimulation circuitry housed within the ICS module;

an implantable speech processor (ISP) module having speech processing (SP) electronic circuitry, a battery, and a microphone all hermetically sealed therein, the ISP module further having an electrical connector that electrically connects first and second conductors through respective first and second feedthru terminals to the SP electronic circuitry; and electrical coupling means for electrically coupling the ICS module with the ISP module through the connector on the ISP module;

wherein the battery within the ISP module provides operating power for both the ISP module and the ICS module, and further wherein sounds sensed through the microphone in the ISP module are electronically processed by the SP electronic circuitry and sent to the ICS module through the coupling means as stimulation signals which may be applied to the electrode contacts on the electrode array.

2. The FICIS of claim 1 wherein the ICS module further includes a clam-shell construction comprising an upper shell, a lower shell, and an inner shell, each shell having a flange around its periphery, the upper and lower shells being of approximately the same size, and the inner shell being smaller than the lower shell so that it readily fits within the upper shell, but with the flange of the inner shell extending out to engage the flanges of the upper and lower shells, wherein the flanges of upper, lower and inner shells are all bonded together, with the inner shell being positioned inside of the lower shell, and wherein the volume between the upper shell and inner shell comprises an hermetically-sealed cavity wherein the stimulation circuitry is housed, and wherein the volume between the lower shell and the inner shell comprises a non-hermetically sealed cavity, and further including a plurality of electrical feedthru terminals having one end extending into the non-hermetically-sealed cavity and the other extending into the hermetically-sealed cavity.

3. The FICIS of claim 2 wherein the electrical coupling means comprises a two-conductor cable attached at one end to the ICS module through respective ones of the plurality of electrical feedthru terminals, said two-conductor cable having a jack at is other end adapted for detachable connection with the electrical connector of the ISP module.

4. The FICIS of claim 3 wherein the ISP module has a channel groove around at least a portion of its periphery edge into which the two-conductor cable that electrically couples the ISP module to the ICS module may be wrapped.

5. The FICIS of claim 2 further including an RF coil secured to one side of the bonded flanges of the upper, lower and inner shells, the RF coil having end wires that connect with the stimulation circuitry through respective ones of the plurality of electrical feedthru terminals.

6. The FICIS of claim 5 wherein the electrical coupling means comprises a two-conductor cable having a jack at one end adapted for detachable connection with the electrical connector of the ISP module, and has an end coil at its other end, wherein the end coil is inductively coupled with the RF coil of the ICS module when the end coil is positioned proximate the RF coil.

7. The FICIS of claim 6 wherein the ISP module has a channel groove around at least a portion of its periphery edge into which the two-conductor cable that electrically couples the ISP module to the ICS module may be wrapped.

8. The FICIS of claim 1 wherein the battery housed within the ISP module comprises a rechargeable battery, and wherein the FICIS further includes an external unit having a power source and an external coil through which battery-charging energy may be coupled to the rechargeable battery of the ISP module through an inductive coupling link established between the external coil and the RF coil of the ICS module and the electrical coupling means between the ICS module and the ISP module.

9. The FICIS of claim 8 wherein the external unit further includes external speech processing means which, when inductively coupled with the ICS module, may selectively assist or override the operation of the ISP module.

10. The FICIS of claim 2 wherein the upper shell of the ICS unit further includes a detent cavity centrally located therein into which a permanent magnet may be removably inserted.

11. The FICIS of claim 10 wherein the upper, lower, and inner shells of the ICS module are made from titanium or an alloy of titanium.

12. A fully implantable cochlear implant system (FICIS) comprising:

an implantable cochlear stimulator (ICS) module having an electrode array attached thereto, the electrode array having a multiplicity of spaced-apart electrode contacts at or near a distal end thereof, each electrode contact having a respective electrical conductor attached thereto, all of the electrical conductors being electrically connected with stimulation circuitry housed within the ICS module;

an implantable speech processor (ISP) module having speech processing (SP) electronic circuitry, a battery, all hermetically sealed therein, the ISP module further having an electrical connector that electrically connects a plurality of conductors through a respective plurality of feedthru terminals to the SP electronic circuitry;

a microphone coupled to the ISP module; and electrical coupling means for electrically coupling the ICS module with the ISP module through the connector on the ISP module;

wherein the battery within the ISP module provides operating power for both the ISP module and the ICS module, and further wherein sounds sensed through the microphone are electronically processed by the SP electronic circuitry and sent to the ICS module through the coupling means as stimulation signals which may be applied to the electrode contacts on the electrode array.

13. The FICIS of claim 12 wherein the electrical coupling means comprises a multi-conductor cable having a multiplicity of conductors attached at one end to the ICS module through respective ones of a multiplicity of electrical feedthru terminals, said multi-conductor cable having a jack at is other end adapted for detachable connection with the electrical connector of the ISP module.

* * * * *